US012608680B2

(12) United States Patent
Kumar

(10) Patent No.: US 12,608,680 B2
(45) Date of Patent: Apr. 21, 2026

(54) COORDINATED MOBILE ACCESS TO ELECTRONIC MEDICAL RECORDS

(71) Applicant: DocBuddy, Inc., Greenwood Village, CO (US)

(72) Inventor: Pradeep Kumar, Bangalore (IN)

(73) Assignee: DocBuddy, Inc., Greenwood Village, CO (US)

( * ) Notice: Subject to any disclaimer, the term of this patent is extended or adjusted under 35 U.S.C. 154(b) by 1014 days.

(21) Appl. No.: 15/681,174

(22) Filed: Aug. 18, 2017

(65) Prior Publication Data

US 2017/0344948 A1 Nov. 30, 2017

Related U.S. Application Data

(63) Continuation of application No. PCT/US2016/018761, filed on Feb. 19, 2016.

(60) Provisional application No. 62/118,041, filed on Feb. 19, 2015.

(51) Int. Cl.
G16H 10/60 (2018.01)
G06Q 10/10 (2023.01)

(52) U.S. Cl.
CPC ............. G06Q 10/10 (2013.01); G16H 10/60 (2018.01)

(58) Field of Classification Search
CPC ...... G06Q 10/10; G06Q 50/24; G06Q 10/107; G16H 10/60; G16H 10/65; G16H 15/00; G16H 50/30; G16H 50/50; G16H 50/70
See application file for complete search history.

(56) References Cited

U.S. PATENT DOCUMENTS

| | | | |
|---|---|---|---|
| 2005/0055246 A1 | 3/2005 | Simon | |
| 2006/0149558 A1* | 7/2006 | Kahn | G10L 15/18 704/278 |
| 2011/0191122 A1* | 8/2011 | Kharraz Tavakol ... | G06Q 10/10 705/2 |
| 2013/0110547 A1* | 5/2013 | Englund | G16H 10/60 705/3 |
| 2013/0262155 A1 | 10/2013 | Hinkamp | |
| 2014/0249831 A1 | 9/2014 | Gallopyn | |
| 2015/0081332 A1* | 3/2015 | Casper | G16H 10/60 705/3 |
| 2016/0357915 A1* | 12/2016 | Morris | G16H 10/60 |

* cited by examiner

*Primary Examiner* — Chad A Newton
(74) *Attorney, Agent, or Firm* — Dorsey & Whitney LLP

(57) ABSTRACT

Embodiments can enable coordinated access to electronic medical records (EMRs) by mobile devices in communication with an EMR coordination server over a communications network, thereby integrating the EMR access into the physician's workflow. The EMR coordination server can receive a schedule request for a physician via the mobile device, and can identify appointments associated with the physician. Each appointment can be associated with a patient, an EMR server identified as having the patient's records, and a network location and EMR schema. The physician can select an appointment to access associated fields. The fields can be populated with fresh data from the identified EMR server, accessed by its network location, and mapped according to its EMR schema. Field data can be updated by physician dictation (or otherwise) and dictated audio can be automatically transcribed. Embodiments can operate even in context of multiple EMR servers having multiple EMR schemas and/or network locations.

1 Claim, 7 Drawing Sheets

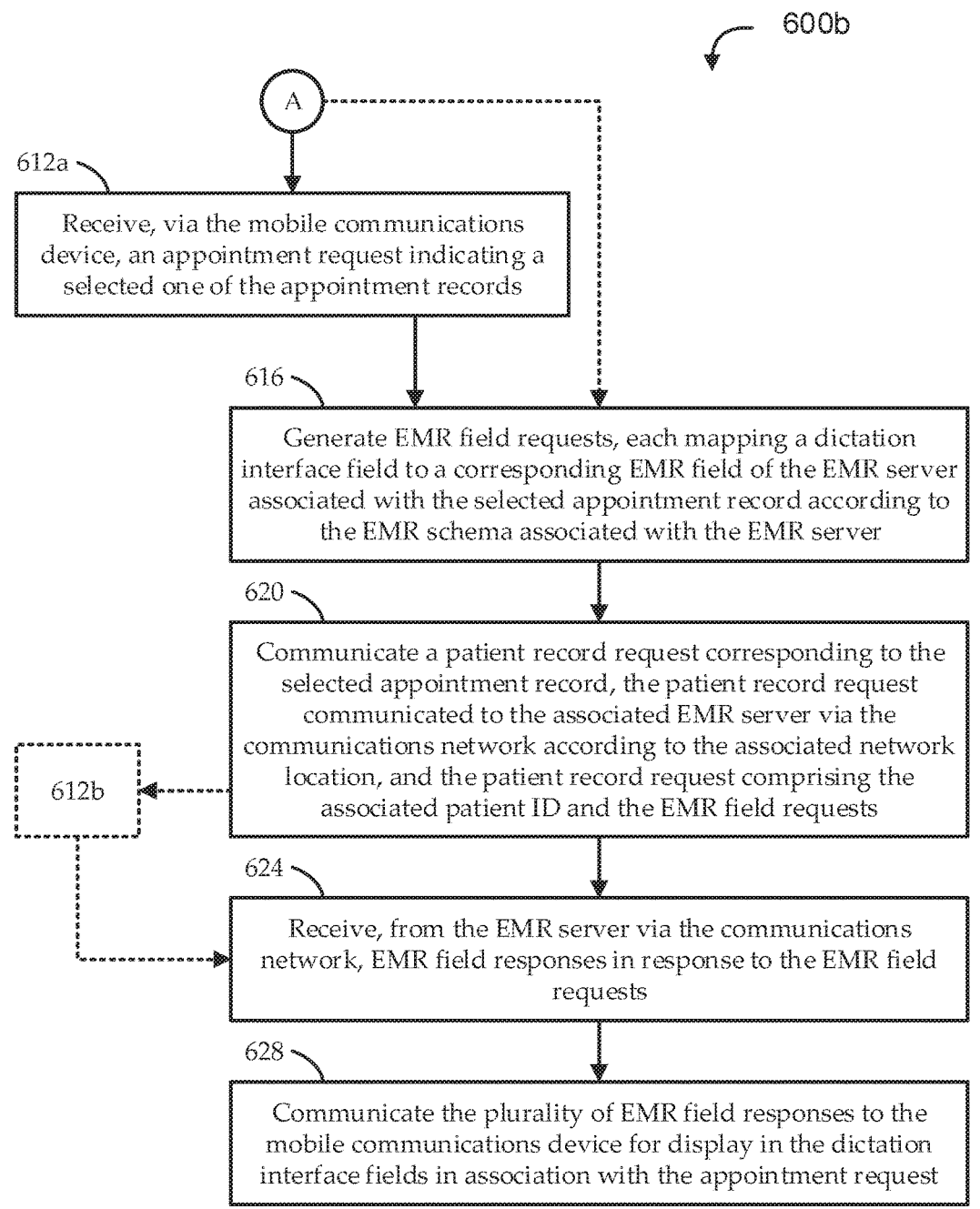

600b

612a
Receive, via the mobile communications device, an appointment request indicating a selected one of the appointment records 616
Generate EMR field requests, each mapping a dictation interface field to a corresponding EMR field of the EMR server associated with the selected appointment record according to the EMR schema associated with the EMR server 620
Communicate a patient record request corresponding to the selected appointment record, the patient record request communicated to the associated EMR server via the communications network according to the associated network location, and the patient record request comprising the associated patient ID and the EMR field requests 612b 624
Receive, from the EMR server via the communications network, EMR field responses in response to the EMR field requests 628
Communicate the plurality of EMR field responses to the mobile communications device for display in the dictation interface fields in association with the appointment request

FIG. 6B

COORDINATED MOBILE ACCESS TO ELECTRONIC MEDICAL RECORDS

CROSS-REFERENCE TO RELATED APPLICATION

This application is a continuation of U.S. PCT Application No. PCT/US2016/018761, entitled, "COORDINATED MOBILE ACCESS TO ELECTRONIC MEDICAL RECORDS," filed on Feb. 19, 2016, which claims priority from U.S. Provisional Application No. 62/118,041, entitled "METHOD AND SYSTEM FOR ELECTRONIC MEDICAL RECORD DICTATION AND TRANSCRIPTION VIA SMARTPHONE," filed on Feb. 19, 2015, the contents of all of which are incorporated herein as if set forth in full.

FIELD

Embodiments relate generally to client-server interactions, and, more particularly, to enabling coordinated access to electronic medical records by mobile devices.

BACKGROUND

In many contexts, physicians and other health care providers can have large numbers of appointments with large numbers of patients. Providing proper care to those patients can involve interacting with (e.g., reading from and writing to) up-to-date medical information for the patients. That medical information is increasingly being maintained in the form of electronic medical records (EMRs), which can be stored in an EMR database server. Interacting with such EMR database servers typically has many limitations. One such limitation is that the EMR databases tend to be slow and prone to crashing, particularly when large numbers of calls are made to the databases and/or when the databases become very large.

Another such limitation is that updating electronic medical records (EMRs) tends to be time consuming and inefficient, and tends to involve multiple parties working together to complete an update. For example, when a physician sees a patient, the physician typically dictates notes and observations into a local audio file record (e.g., on a voice recorder, a computer, etc.). Periodically, the local audio files can be given to a manual transcription service, or processed through transcription software, for conversion of the dictated audio notes into text notes. The notes are then compared to predetermined record categories to determine the proper entry location for each of the notes. The transcribed notes can then be manually copied to appropriate fields for digitally storage in proper locations in the patient's EMR. This is typically a multistep process involving at least three or four different individuals and steps, each of which taking time and resources, and potentially introducing errors and other inefficiencies.

Yet another limitation of current EMR approaches is that different EMR providers tend to store EMRs according to different schema and tend to provide different types of interfaces to the data. This can place a number of undesirable constraints on EMR usage. For example, the multiple proprietary formats can limit the portability of a patient's data from one health care provider to another. Further, extensive training can be involved before using the often-cumbersome user interface applications, which can force providers to use dedicated staff and to add steps to their data entry and access processes. Even further, some physicians and other providers work in multiple locations (e.g., one doctor may have hospital privileges at multiple hospitals, in addition to a private practice), and could potentially have patients with EMRs stored in different EMR systems and/or server locations.

For these and other reasons, day-to-day interactions with patient EMRs tend to be inefficient, error-prone, and poorly integrated with routine workflows of health care providers.

BRIEF SUMMARY

Among other things, systems and methods are described herein for enabling coordinated access to electronic medical records (EMRs) by mobile devices. Some embodiments are described in context of a client interface device (e.g., a mobile phone, tablet computer, etc.) in communication with an EMR coordination server over a communications network. The EMR coordination server is in communication with EMR servers that store EMRs for large numbers of patients associated with multiple physicians. Embodiments of the EMR coordination server can enable efficient real-time coordination of the client interface device with one or more EMR servers of one or more EMR types (e.g., EMR data schemas) in one or more locations, thereby efficiently integrating the EMR access into the physician's workflow.

For example, the EMR coordination server can receive a schedule request associated with a physician identifier (associated with an authenticated physician) via the physician's mobile device. In response to the schedule request, the EMR coordination server can identify appointment records in an appointments database (e.g., at the mobile device, at the EMR coordination server, at one or more EMR servers, etc.) as associated with the physician identifier. Each appointment record can be further associated with a patient identifier and a network location of an EMR server having the patient's EMR stored thereon. Each EMR server can also be associated with an EMR schema (defining fields, data types, and/or other information relating to how the EMRs are stored in that EMR server). The identified appointment records can be communicated to the mobile device and used to display an appointment schedule to an interface screen. When the physician selects one of the displayed appointments, a number of predefined dictation interface fields can be displayed. It is desirable for the dictation fields include fresh data from the EMR servers. Accordingly, some implementations generate EMR field requests (e.g., in response to receiving one or more appointment requests from the mobile device), each mapping one of the dictation interface fields to a corresponding EMR field of the EMR server associated with the selected appointment record according to the EMR schema associated with the EMR server. At least one patient record request can be issued corresponding to the selected appointment record, the patient record request communicated to the associated EMR server via the communications network according to the associated network location, and the patient record request comprising the associated patient identifier and the EMR field requests. EMR field responses can be received from the EMR server (via the communications network) in response to the EMR field requests, and the EMR field responses can be communicated to the mobile device for display in the dictation interface fields in association with the appointment request. The dictation fields can then display fresh data from the EMR server.

BRIEF DESCRIPTION OF THE DRAWINGS

The present disclosure is described in conjunction with the appended figures:

FIGS. 6A and 6B show a flow diagram of an illustrative method for interfacing with EMR over a communications network, according to various embodiments.

In the appended figures, similar components and/or features may have the same reference label. Further, various components of the same type may be distinguished by following the reference label by a second label that distinguishes among the similar components. If only the first reference label is used in the specification, the description is applicable to any one of the similar components having the same first reference label irrespective of the second reference label.

DETAILED DESCRIPTION

In the following description, numerous specific details are set forth to provide a thorough understanding of various embodiments. However, one having ordinary skill in the art should recognize that the invention can be practiced without these specific details. In some instances, circuits, structures, and techniques have not been shown in detail to avoid obscuring embodiments.

Figure 1:
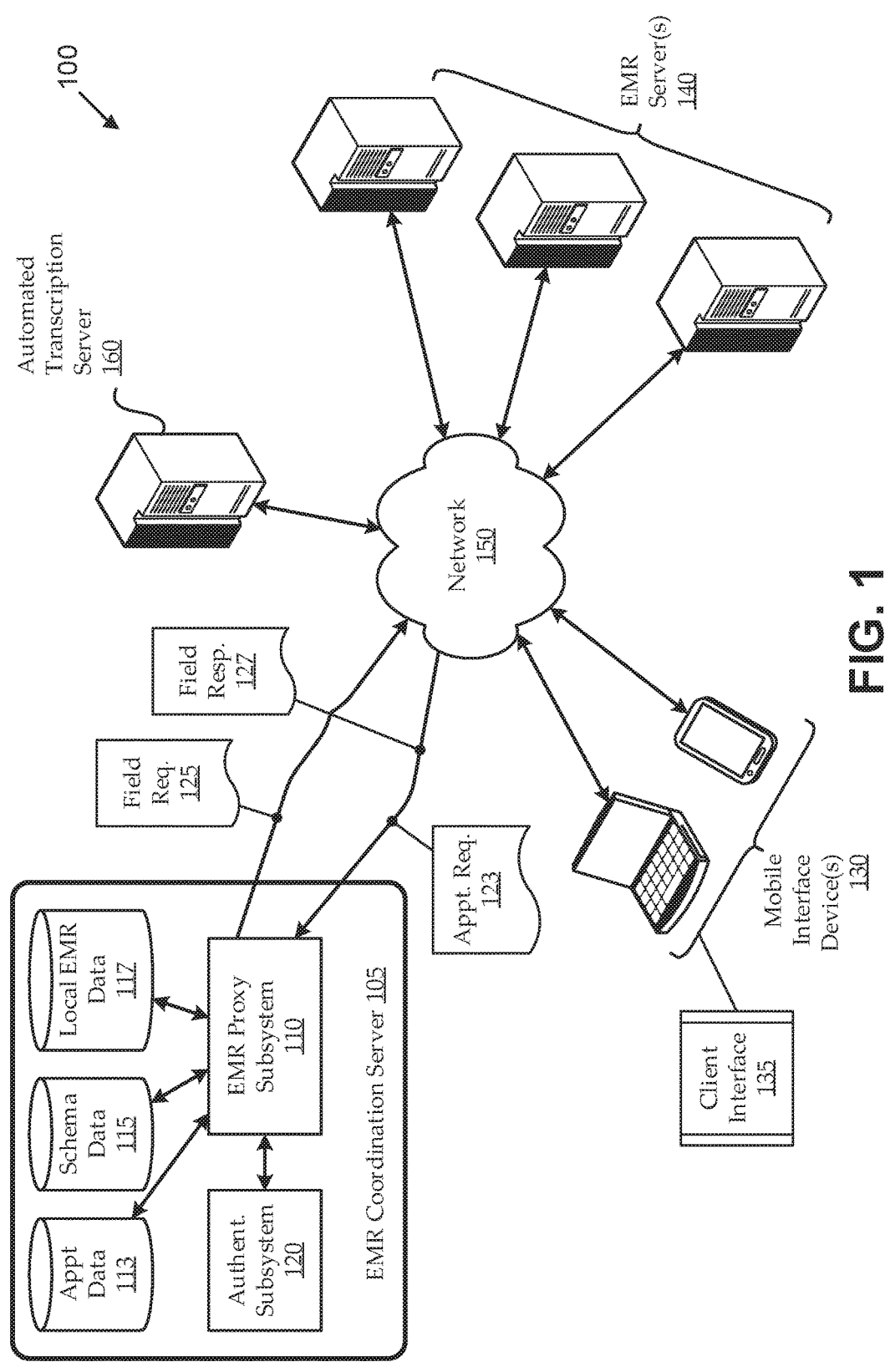
FIG. 1 shows an illustrative electronic medical records (EMR) environment, according to various embodiments.

Turning first to FIG. 1, an illustrative electronic medical records environment 100 is shown, according to various embodiments. The environment 100 includes an EMR coordination server 105 in communication with one or more mobile interface devices 130 and one or more EMR servers 140 over a communications network 150. The communications network 150 can include any suitable communications links, such as wired and/or wireless, public and/or private, secured and/or unsecured, local and/or remote, and/or other communications links. In some implementations, the communications network 150 includes the Internet. The mobile interface devices 130 can include any suitable mobile devices that provide both user interface functionality (e.g., via a touchscreen, keyboard, etc.) and network interface functionality (e.g., wireless network ports, antennas, protocols, etc.). For example, the mobile interface devices 130 can include smart phones, laptop computers, tablet computers, and the like.

Physicians and other health care providers tend to have large numbers of appointments with large numbers of patients. For example, the physician may work in private practice, in a practice group with multiple locations, in one or more hospitals, etc. Providing proper care to those patients can involve accessing, updating, and/or otherwise interacting with accurate and up-to-date medical information for those patients. That medical information is increasingly being maintained in the form of electronic medical records (EMRs), which can be stored in an EMR database server. As used herein, EMR is intended broadly to include any type of electronic patient care records, including those referred to in the relevant art as EMR, electronic health records (EHR), and the like. Presently, there are hundreds of EMR vendors, though it has been estimated that roughly 90 percent of the market share is served by the top ten vendors. Still, many of the EMR vendors use their own proprietary schemas for defining how the EMR data is stored in their systems (in their EMR servers 140), including supported data types, data fields, database architectures, etc.

Interacting with the EMR servers 140 of these different EMR vendors can have many limitations, which have tended to frustrate the integration of EMRs into the daily routines and workflows of physicians. One such limitation is that the EMR databases tend to be slow and prone to crashing, particularly when large numbers of calls are made to the databases and/or when the databases become very large. For example, upgrading and/or migrating data on the EMR servers 140 can be costly and rife with privacy and security concerns, which, among other concerns, has kept many health care facilities from exploiting advancements in hardware and software.

Another such limitation is that updating EMRs tends to be time consuming and inefficient, and tends to involve multiple parties working together to complete an update. For example, when a physician sees a patient, the physician typically dictates notes and observations into a local audio file record (e.g., on a voice recorder, a computer, etc.). Periodically, the local audio files can be given to a manual transcription service, or processed through transcription software, for conversion of the dictated audio notes into text notes. The notes are then compared to predetermined record categories to determine the proper entry location for each of the notes. The transcribed notes can then be manually copied to appropriate fields in the patient's EMR. This is typically a multistep process involving at least three or four different individuals and steps, each of which taking time and resources, and potentially introducing errors and other inefficiencies.

Such inefficiencies can be exacerbated by the fact that different EMR providers often use different schema for storing EMRs and provide different types of user interfaces to the EMR servers 140. For example, each EMR system can have its own proprietary software interface with which to access the EMR data from the EMR servers 140, and each different proprietary interface can include different capabilities and different data arranged in different ways (e.g., on different screens or tabs, in different fields, identified with different nomenclature, etc.). Accordingly, interactions with the EMR servers 140 are often limited to specially trained personnel, which typically removes the physicians from direct interaction with their patient's records. Further, the proprietary interfaces also tend to be slow, non-intuitive, and error-prone, which adds to the inefficiencies of EMR access. The proprietary schema, staff training, etc. often make it expensive, and otherwise difficult, for health care providers to change their EMR provider.

Use of different EMR systems by different health care providers can have additional, undesirable impacts. For example, differences between the EMR systems (e.g., the different schema) can tend to limit the portability of a patient's data from one health care provider to another when the providers use different EMR systems. Additionally, some physicians and other providers work in multiple locations (e.g., one doctor may have hospital privileges at multiple hospitals, in addition to a private practice), and can potentially have patients with EMRs stored in different EMR systems and/or server locations. This can further affect the physician's ability to access and/or update patient EMRs, which can further frustrate the integration of those EMRs into the physician's daily routine and/or workflow.

Embodiments described herein seek to improve integration of EMRs into physician workflows by enabling efficient, coordinated, real-time access to EMR servers 140 via mobile interface devices 130. The EMR coordination server 105 can provide a number of features to that end. For example, embodiments of the EMR coordination server 105 can enable real-time access to, and updating of, EMR servers 140 by large numbers of physicians without overtaxing the EMR servers 140 (e.g., without causing the EMR servers 140 to crash) and without training the physicians on proprietary EMR software interfaces. Embodiments enable such features, even in context of multiple EMR servers 140 having different schema and/or in different network locations.

As illustrated, embodiments of the EMR coordination server 105 include an EMR proxy subsystem 110, an authentication subsystem 120, and one or more data stores (e.g., some or all of an appointment data store 113, a schema data store 115, and a local EMR data store 117). In some embodiments, each mobile interface device 130 has an instance of a client interface application 135. The client interface application 135 can be any suitable type of application, including a specialized, self-contained software application ("app"), a thin client application, etc. The client interface application 135 provides front-end graphical user interface functionality and back-end communications functionality, including for enabling communications of EMR data via the EMR coordination server 105. In some embodiments, the client interface application 135 and the EMR coordination server 105 communicate as client and server computers, respectively. For example, the EMR coordination server 105 can effectively act as a proxy to the mobile interface devices 130 by controlling data exchanges between the client interface applications 135 and the EMR servers 140 via the communications network 150.

In some implementations, all communications with the EMR coordination server 105 are handled by the EMR proxy subsystem 110. For example, some implementations require that a physician be authenticated prior to permitting access to patient EMR data. As used herein, "physician" is intended broadly to include any user of the client interface application 135. For example, the user (i.e., "physician") can be a certified doctor, nurse, health care provider, or anyone else permitted to access EMR data. Prior authentication can be a requirement imposed by organization, by usage agreement, by statute (e.g., under the Health Insurance Portability and Accountability Act of 1996 (HIPAA), etc.), etc. The client interface application 135 can enable authentication of the physician by receiving physician credentials. The credentials can be received in any suitable manner, for example, by prompting for a user name and password, by tying authentication to possession of the mobile interface device 130, by receipt of one or more biometrics, by optical or wireless recognition of a credential, etc. In some embodiments, the credentials and/or other authentication information can be communicated, via the communications network 150, to the authentication subsystem 120 of the EMR coordination server 105 (e.g., via the EMR proxy subsystem 110).

Figure 2:
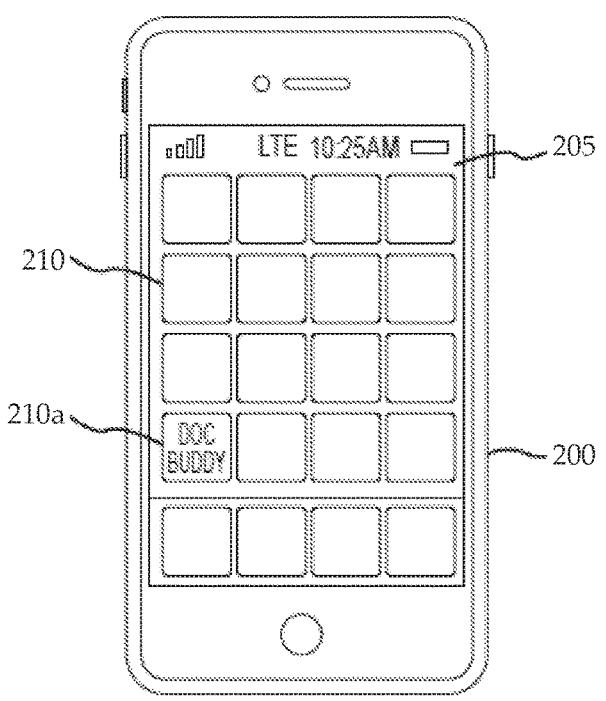
FIG. 2 shows an illustrative graphical interface (e.g., a home screen) of a smart phone having a number of application icons displayed thereon.

For the sake of illustration, FIG. 2 shows an illustrative graphical interface 205 (e.g., a home screen) of a smart phone 200 having a number of application icons 210 displayed thereon. One of the icons 210*a* is associated with a DocBuddy™ app. For example, the operating system of the smart phone 200 can call and execute the DocBuddy™ app when a physician touches the associated icon 210*a*. Some implementations of the DocBuddy™ app, when executed, prompt the user for credentials.

Figure 3:
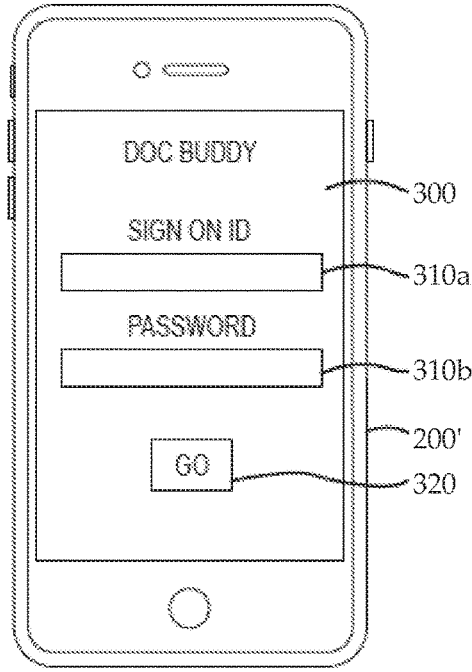
FIG. 3 shows a sign-on screen on an illustrative smart phone having defined spaces and for entry of a user identifier and user password, respectively.

For example, FIG. 3 shows a sign-on screen 300 on an illustrative smart phone 200' having defined spaces 310*a* and 310*b* for entry of a user identifier and user password, respectively. For example, a user touches one of the spaces 310, and an on-screen keyboard pops up for entry of the letters and numerals required. A "GO" icon 320 is displayed beneath the sign-on spaces 310. When the user touches the "GO" icon 320, the app can execute an authentication routine. For example, the app can locally verify that the provided credentials are valid, the app can communicate the credentials to the authentication subsystem 120 over the communications network 150, etc. Some implementations provide separate app login credentials and EMR access credentials. For example, some implementations permit a physician to log into the application with first credentials to view an appointment schedule, to perform offline functions, etc.; but requires further authentication from the authentication subsystem 120 (e.g., using the same or different credentials) prior to permitting transfer of EMR data to and/or from the mobile interface device 130.

Returning to FIG. 1, the authentication subsystem 120 can include, or be in communication with, a database of authorized physicians. For example, the authorized physicians can be physicians that previously registered with the EMR proxy subsystem 110, with one or more EMR servers 140, with the client interface application 135, or in any other suitable manner. Some implementations associate each registered physician with a set of access privileges. For example, the access privileges can indicate whether a particular physician is authorized to access particular EMR servers 140, particular patient records, particular types of EMR data, etc. In some implementations, the registration can further associate a particular physician with additional information, such as user preferences, scheduling preferences, contact information, association information (e.g., whether the physician is associated with one or more health care organizations; whether the physician is associated with other physicians for referrals, for access to their patients' records, etc.; etc.), and/or any other suitable information. Successful authentication can effectively tie a physician's usage of the client interface application 135 with a registered physician identifier. As described herein, various features and functions enabled by the EMR coordination server 105 can be performed according to the physician identifier.

Notably, features of various embodiments rely on communication of patient medical information over the communications network 150. HIPAA and/or other regulations (e.g., including other governmental regulations, privacy policies, etc.) may place certain requirements and/or restrictions on the transfer of such patient data. Embodiments of the EMR proxy subsystem 110 can establish secure links (e.g., persistent connections, secure tunnels, etc.) with the EMR servers 140 and with the client interface applications 135 of the mobile interface devices 130, and those secure links can be implemented to satisfy any desired and/or imposed requirements and/or restrictions for sensitive data transfer. Authentication by the authentication subsystem 120 can be a precondition of the EMR proxy subsystem 110 establishing a secure connection with the client interface application 135. Alternatively, authentication can be a precondition of communicating sensitive information over the communications network 150 between the EMR proxy subsystem 110 and the client interface application 135.

Further, some implementations can encrypt and/or otherwise secure transferred EMR data (and/or other sensitive data), as desired.

For the sake of context, it is helpful to describe a typical physician workflow as it relates to interactions with the EMR coordination server 105 via the physician's mobile interface device 130. The physician can typically call, and log into, the app via a graphical interface of the mobile interface devices 130 (e.g., as illustrated in FIGS. 2 and 3). The physician can then pull up a schedule (e.g., for the day), which can include a number of appointments. Some or all of the appointments can indicate a time during which the physician is scheduled to see a particular patient (or patients). If the physician selects one of the appointments from the schedule, a number of predetermined field identifiers can be displayed (e.g., along with any other suitable information, such as other information from the patient's file, geographic location of the appointment, etc.). Some implementations can display the field identifiers in a manner that indicates additional information (e.g., color, typeface, icons, text fields, etc.), such as, whether the associated field already contains EMR information for the patient, whether the associated field has been sufficiently completed, whether the field contains errors, when was the last time the associated field was updated, whether the associated field has been successfully updated from an associated EMR server 140, etc. When the physician selects one of the field identifiers, a field data interface can be displayed for the associated field. The field can be automatically populated with updated information from the EMR server 140 where that patient's EMR is being stored (e.g., after appropriate schema mapping and/or other processing, as described below). The physician can use dictation and/or other data entry tools to add and/or change patient information associated with the selected field. The updated patient information can then be submitted by the physician (through the same interface) and uploaded back to the associated EMR server 140 (e.g., after pre-processing, after mapping according to the associated EMR schema, etc.). In this way, the physician can integrate up-to-date patient EMR information from EMR servers 140 substantially in real time within the physician's workflow.

Figure 4:
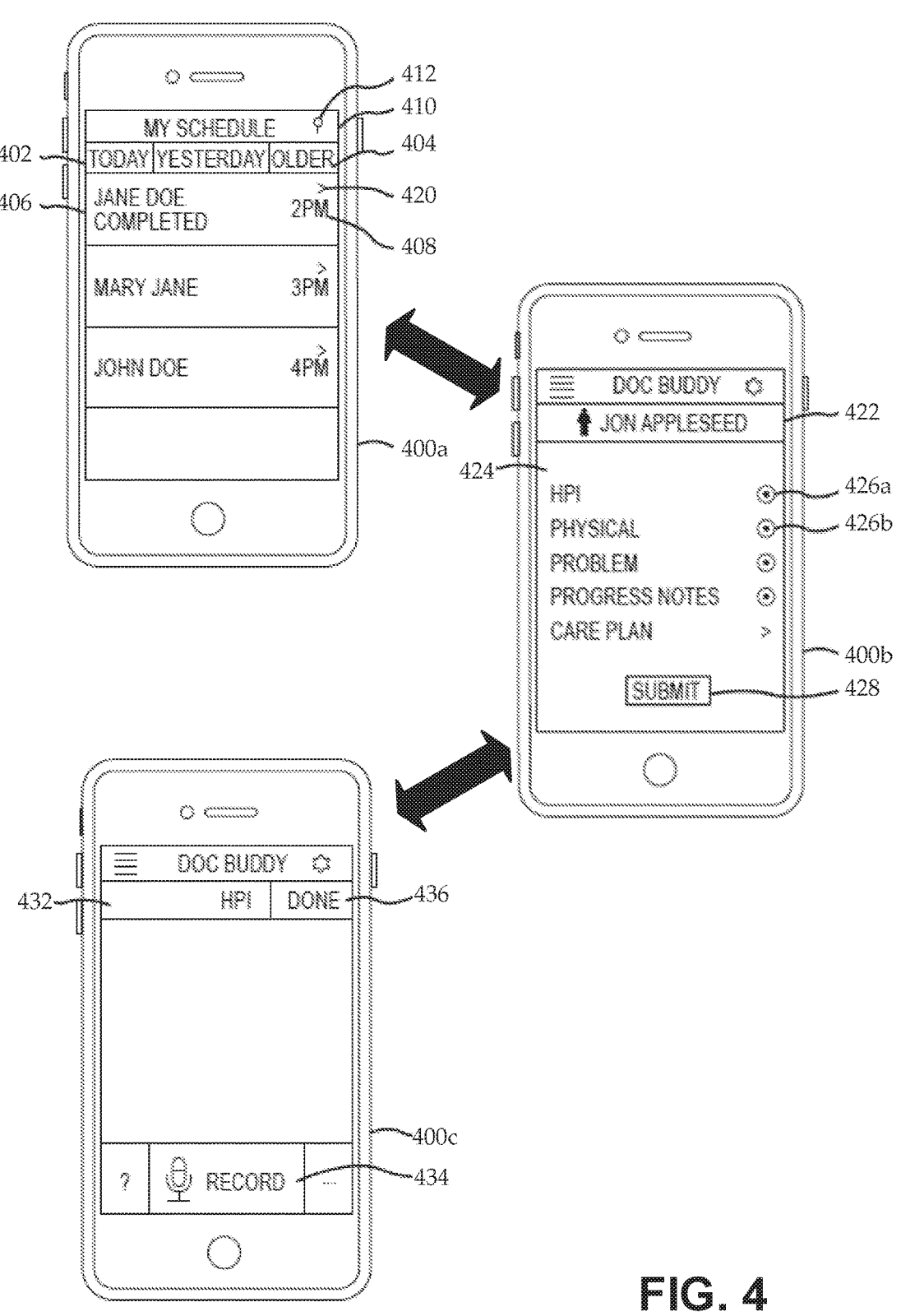
FIG. 4 shows an illustrative application interface implemented on an illustrative smart phone.

For the sake of further illustration, FIG. 4 shows an illustrative application interface implemented on an illustrative smart phone 400. A first smart phone 400a is shown with an illustrative schedule interface screen displayed. A header box 410 displays the user's (e.g., physician's) name and includes selectable blocks 402 for "Today," "Yesterday," and "Older," (and/or any suitable other designations, such as "Upcoming," "Next Two Days," "Past Two Days," etc.) associated with the physician's patient appointment schedule. The patient schedule for today can be selected by default, and the user can select a different schedule, as desired. For example, when "Older" schedule 404 is selected, a date query can pop up to permit the user to input a desired date for retrieval of the patient appointment schedule for the selected timeframe. Some implementations also include additional navigation and/or other controls. For example, a search icon 412 can be provided, and selecting the search icon 412 can provide a searchable listing of patients and/or other contacts, and/or any other suitable information. Below the header block 410 is an appointment listing 406 (e.g., chronological, or grouped, filtered, etc. in any other suitable manner) that can include information, such as the associated patient's name, appointment time 408, a selectable icon 420, appointment location, appointment status, and/or any other useful information. When the physician selects the appointment (e.g., by touching the selectable icon 420), a corresponding appointment screen can be displayed.

A second smart phone 400b is shown with an illustrative appointment interface screen displayed (e.g., corresponding to one of the appointments on the schedule interface screen). The appointment interface screen can include a header block 422, which can provide information, such as patient name, patient photo, appointment location, referring physician, etc. The appointment interface screen can further include a series of selectable field identifiers 424 and/or other categories (e.g., with interactive buttons 426 or other navigation controls, from which the user can make a selection). For the sake of illustration, five field identifiers are shown: "HPI" (History of Present Illness), "Physical," "Problem," "Progress Notes," and "Care Plan." As described herein, each of these field identifiers can be mapped (e.g., by the EMR proxy subsystem 110) to a corresponding field of an EMR server 140 according to an associated EMR schema (e.g., as stored by the schema data store 115).

For example, if the physician selects the "HPI" field identifier 424, this can indicate the physician's desire to view and/or modify information relating to the patient's HPI. In response to the selection, a corresponding field interface screen can appear. For example, a third smart phone 400c is shown with an illustrative field interface screen displayed (e.g., corresponding to the selected field identifier 424 on the appointment interface screen). The field interface screen can include a header block 432, which can indicate any suitable information, such as a title for the field, appropriate subject matter for dictation, etc. Some implementations further include a "Done" button 436, or the like. The field interface screen can also include dictation controls, such as a "Record" button 434, and a data entry field. When the physician touches the Record button 434, recording can begin. As illustrated in FIG. 1, some implementations include an automated transcription server 160 in communication with the EMR coordination server 105 and/or the mobile interface devices 130 via the communications network. The automated transcription server 160 can be comprised by, or separate from, the EMR coordination server 105. For example, the physician's dictation audio can be communicated (e.g., after completion of the dictation, or substantially in real time) to an automated transcription server 160 (and/or any other suitable dictation-to-text processing), which can convert the audio into text. The dictated text can then appear in the field interface screen (e.g., in a space below the header block 432). Some implementations use a specialized transcription processor that is adapted to recognize medical transcription, such as a cloud-based, computer-implemented medical transcription service. Other controls can be provided on the field interface screen. For example, during recording, recording controls can be displayed (e.g., stop, pause, playback, etc.); and/or touching a data field can cause a virtual keyboard or other interface to appear. Further, the interface can include guides, such as specific mandatory and/or optional sub-fields, suggested content to dictate, templates (e.g., checklists) or other reminders, etc.

When the physician completes data entry (e.g., when finished with the dictation), the physician can determine whether the field is complete. For example, the physician can check the text, the physician can review the audio, automated pre-processing can be performed, etc. Pre-processing the updated patient data can include checking for errors. For example, implementations can include simple processing (e.g., checking for blank fields, spelling errors, audio quality, etc.) and/or complex processing (e.g., checking for missing expected information, inconsistent diagnoses, incorrect prescriptions and/or dosages, suspect treatment plans, etc.). Such pre-processing can be performed by natural language processing, text parsing, and/or in any suitable manner. In some implementations, some or all pre-processing is performed after the audio is converted to text (i.e., the converted text is analyzed for errors, etc.). When the data entry is complete, the physician can touch the "Done" button 136.

Some implementations can revert to the appointment interface screen. The physician can then select again from the field identifiers 424, and can continue to view and/or input data into corresponding fields. Having completed data entry for one or more fields, some embodiments can locally cache the dictated text and/or audio for subsequent communication to the EMR proxy subsystem 110 over the communications network 150. Alternatively, embodiments can immediately communicate the data to the EMR proxy subsystem 110 over the communications network 150 (e.g., subject to network availability) for remote caching, for example, in the local EMR data store 117 of the EMR coordination server 105. Embodiments of the appointment interface screen can include a "Submit" button 428, or the like. Touching the Submit button 428 can indicate to the client interface application 135 that cached patient data is ready to be submitted to the appropriate EMR server(s) 140. For example, the data can be communicated as a batch transfer, or in any suitable manner. Alternatively, the data can be communicated automatically (i.e., not on-demand by the user), for example, periodically, as it is collected, as network resources become available, etc. In some implementations, the updated (e.g., and pre-processed) patient data can be uploaded back to the appropriate server 140 after being re-mapped to appropriate fields and data types according to the associated EMR schema.

While the workflow described above provides a number of features, many such features relate to real-time, coordinated communication of patient EMR information between the EMR servers 140 that store the data and the physicians that use and update the data (via their mobile interface devices 130). As described herein, such real-time, coordinated communication is enabled by the EMR coordination server 105, and, more particularly, the EMR proxy subsystem 110. Embodiments of the EMR proxy subsystem 110 can include communications input and output ports communicatively coupled with the communications network 150.

The communications output port can transmit a patient record request to an identified EMR server 140 according to a network location (e.g., Internet Protocol (IP) address) of the identified EMR server 140 (the identified EMR server can be identified as having stored thereon an EMR associated with a patient identifier of the patient record request). The patient record request can include multiple EMR field requests 125, each generated by mapping one of a number of dictation interface fields (e.g., defined by the client interface application 135) to a corresponding EMR field of the identified EMR server 140. The mapping can be according to one of a number of EMR schemas stored at the EMR schema data store 115 in association with the identified EMR server 140. For example, the EMR proxy subsystem 110 can be in communication with multiple EMR servers 140, and some of those EMR servers 140 can be associated with different EMR suppliers that use different storage schema (e.g., data types, fields, etc.) for storing the EMR data. Each EMR schema can be an application program interface (API) or other schema that effectively maps each desired field of the client interface applications 135 to a corresponding one or more fields of a particular type of EMR system (e.g., provided by a particular EMR vendor, etc.). The patient record request can correspond to an appointment request 123 received from a mobile communications device. For example, the received appointment request 123 can indicate a selected one of multiple appointment records stored at the appointment data store 113 in association with a physician identifier and a patient identifier. The communications input port can receive EMR field responses 127 from the identified EMR server 140 in response to the transmitted EMR field requests 125. Some embodiments of the communications output port of the EMR proxy subsystem 110 can transmit the EMR field responses 127 to the mobile interface device 130 for display in the dictation interface fields by the client interface application 135.

In some embodiments, the appointment request 123 can be associated with a prior schedule request. The communications input port can receive a schedule request associated with the physician identifier from the mobile communications device; and the communications output port can transmit appointment records to the mobile communications device in response to the schedule request. For example, as described above, upon successful login (or upon otherwise accessing a schedule interface screen), embodiments can submit a schedule request to a local schedule store, a remote schedule store at the EMR coordination server 105, one or more remote schedule stores in one or more EMR servers 140, etc. The appointment records can be received and displayed by the client interface application 135 in response to the schedule store.

As described above, some embodiments further include an authentication subsystem 120. The authentication subsystem 120 can include any suitable type of authentication, such as single-factor, multi-factor, password-based, biometric based, and/or other authentication. While the authentication subsystem 120 is shown as part of the EMR coordination server 105, some or all functions of the authentication subsystem 120 can be implemented in the client interface applications 135 and/or otherwise on the mobile interface devices 130. In some implementations, credentials used to access the mobile interface devices 130 (e.g., a passcode, fingerprint, etc.) can be used as credentials for automatically authenticating use of the client interface applications 135. In other implementations, the client interface applications 135 include one or more types of authentication, including one or more interface screens for receiving credentials. In some such implementations, the received credentials can be authenticated locally; and in other such implementations, the received credentials can be communicated to the authentication subsystem 120 in the EMR coordination server 105 for authentication. Some implementations include multiple levels of authentication. For example, the client interface applications 135 can locally receive credentials and authorize use of the client interface applications 135 itself (e.g., for schedule access, etc.). Those or other credentials can also be communicated to the authentication subsystem 120 of the EMR coordination server 105 for association with a physician identifier (e.g., an email address, a physician license number, or any other suitable identifier). The physician identifier can then be used by the authentication subsystem 120 to permit or deny access to patient records in one or more EMR servers 140. For example, local authentication may permit access to an appointments list, but no sensitive data will be included in any fields or interface screens of the client interface applications 135 until and unless the user is further authorized to access each applicable EMR server 140. In one implementations, local authentication permits access only to data on the app; while further authentication (e.g., according to an email address tied to one or more organization codes) is needed for access to EMR server 140 data (e.g., EMR data and/or schedules and appointments stored by the EMR servers 140). Alternatively, the application may provide almost no functionality until full authentication is received.

As described above, some features increase efficiency of data entry into patient EMRs by using automated transcription of dictated information. For example, when an authenticated physician accesses an appointment via the client interface application 135, a set of field identifiers can be displayed. By selecting a field identifier, a field interface screen can be displayed, which can include dictation controls. The physician can dictate audio into appropriate one or more fields, and the audio can be transcribed into text (e.g., substantially in real time as it is being dictated, after recording completion, etc.). For example, some implementations include an automated transcription server 160 in communication with the EMR coordination server 105 and/or the mobile interface devices 130 via the communications network. Alternatively, the automated transcription server 160 can be comprised by the EMR coordination server 105. Some implementations use a specialized transcription processor that is adapted to recognize medical transcription, such as a cloud-based, computer-implemented medical transcription service. For example, such specialized transcription processors can include medical dictionaries, custom dictionaries for the physician, and/or other tools to assist the automated transcription server 160 in recognizing medical dictation. In some embodiments, the automated transcription server 160 includes transcription input and output ports that are communicatively coupled with the communications network 150 (e.g., over secure communications links). The transcription input port can receive dictation audio (e.g., a dictation file or files) from the mobile interface devices 130 directly and/or via the EMR proxy subsystem 110 (e.g., which may perform one or more types of processing prior to communicating the audio to the automated transcription server 160). The transcription output port can transmit a transcription file back to the mobile interface device 130 (e.g., directly and/or via the EMR proxy subsystem 110). For example, the automated transcription server 160 can use one or more transcription processors, dictionaries, etc. to generate the transcription file as a textual transcription of audio data of the dictation file. In some implementations, each dictation and transcription file includes only a small fraction of a dictation (e.g., one or more words, a phrase, etc.), so that the transcribed textual information can appear in the field of the client interface application 135 substantially as it is being dictated.

Figure 5:
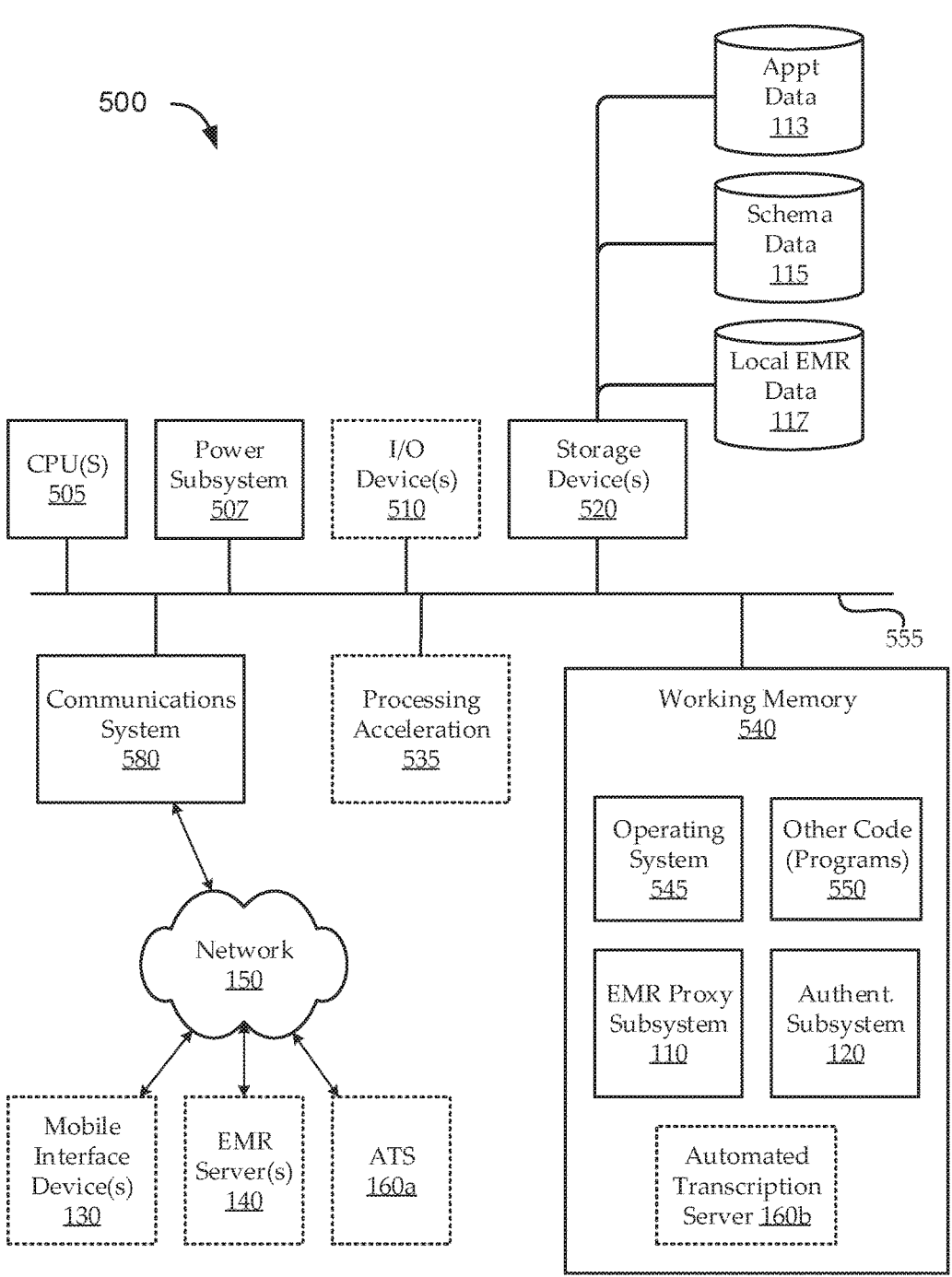
FIG. 5 shows an exemplary computational environment for implementing real-time, coordinated EMR access as described herein, according to various embodiments.

FIG. 5 shows an exemplary computational environment 500 for implementing real-time, coordinated EMR access as described herein, according to various embodiments. For example, the computational environment 500 can be an implementation of some or all of an EMR coordination server 105. The computational environment 500 can be implemented as or embodied in single computer systems, distributed computer systems, or in any other useful way. The computational environment 500 is shown including hardware elements that may be electrically coupled via a bus 555. The hardware elements may include one or more central processing units (CPUs) and/or other processor(s) 505. In some embodiments, the computational environment

500 can also include a processing acceleration unit 535, which can include graphics, communications, and/or other acceleration hardware and/or software. Some or all of the components can be powered by a power subsystem 507, including any suitable power storage, power electronics, power interfaces, etc. Implementations can also include one or more input/output devices 510. For example, the input/output devices 510 can include, and/or be in communication with one or more display devices, communications ports, user interface devices, etc.

Some implementations can permit data to be exchanged, via a communications subsystem 580, with one or more networks and/or any other computer or external system. The communications subsystem 580 can include a modem, a network card (wireless or wired), an infrared communication device, and/or any other suitable components or combinations thereof. In some implementations, the communications subsystem 580 permits communications between the computational environment 500 and one or more mobile interface devices 130, EMR servers 140, and/or automated transcription servers 160 via one or more communications networks 150. Some implementations use the communications subsystem 580 to facilitate distributed processing over multiple computational environments.

The computational environment 500 can also include one or more storage devices 520. By way of example, storage device(s) 520 may be disk drives, optical storage devices, solid-state storage device such as a random access memory (RAM) and/or a read-only memory (ROM), which can be programmable, flash-updateable and/or the like. Some implementations further include computer-readable storage media readers, which can further be connected to a computer-readable storage medium, together (and, optionally, in combination with storage device(s) 520) comprehensively representing remote, local, fixed, and/or removable storage devices plus storage media for temporarily and/or more permanently containing computer-readable information. As illustrated, the storage devices 520 can include, and/or provide access to, an appointment data store 113, a schema data store 115, and a local EMR data store 117.

In some embodiments, the computational environment 500 can also include software elements, shown as being currently located within a working memory 540, including an operating system 545 and/or other code 550, such as an application program (which may be a client application, web browser, mid-tier application, etc.). For example, embodiments can be implemented as instructions, which, when executed by one or more processors 505, cause the processors 505 to perform certain functions. Such functions can include functionality of the EMR proxy subsystem 110, for example, as described above. Some implementations can further provide functionality of the authentication subsystem 120 and/or a local automated transcription server 160*b*.

One embodiments of the computational environment 500 includes the communications system 580 (e.g., a communications port, etc.) in secure communication with the mobile interface devices 130 and the set of EMR servers 140 over the communications network 150; the one or more processors 505; and the working memory 540, including a non-transient computer-readable storage medium having stored thereon a set of instructions, which, when executed, cause the processor to perform steps. The steps can include, at least: receiving, via a mobile communications device, a schedule request associated with a physician identifier; identifying, in response to the schedule request, a plurality of appointment records in an appointments database as associated with the physician identifier, each appointment record further associated with a patient identifier, and a network location of an EMR server having stored thereon an EMR associated with the patient identifier, wherein the EMR server is associated with an EMR schema; receiving, via the mobile communications device, an appointment request indicating a selected one of the appointment records; generating a plurality of EMR field requests, each mapping one of a plurality of dictation interface fields to a corresponding EMR field of the EMR server associated with the selected appointment record according to the EMR schema associated with the EMR server; communicating a patient record request corresponding to the selected appointment record, the patient record request communicated to the associated EMR server via the communications network according to the associated network location, and the patient record request comprising the associated patient identifier and the plurality of EMR field requests; receiving, from the EMR server via the communications network, a plurality of EMR field responses in response to the plurality of EMR field requests; and communicating the plurality of EMR field responses to the mobile communications device for display in the dictation interface fields in association with the appointment request A software module can be a single instruction, or many instructions, and can be distributed over several different code segments, among different programs, and across multiple storage media. Thus, a computer program product may perform operations presented herein. For example, such a computer program product may be a computer readable tangible medium having instructions tangibly stored (and/or encoded) thereon, the instructions being executable by one or more processors to perform the operations described herein. The computer program product may include packaging material. Software or instructions may also be transmitted over a transmission medium. For example, software may be transmitted from a website, server, or other remote source using a transmission medium such as a coaxial cable, fiber optic cable, twisted pair, digital subscriber line (DSL), or wireless technology such as infrared, radio, or microwave.

Alternate embodiments of a computational environment 500 may have numerous variations from that described above. For example, customized hardware might also be used and/or particular elements might be implemented in hardware, software (including portable software, such as applets), or both. Further, connection to other computing devices such as network input/output devices may be employed. Software of the computational environment 500 may include code 550 for implementing embodiments as described herein. For example, while not shown as part of the working memory 540, certain functionality of other subsystems can be implemented with any suitable combination of hardware and software, including using code 550 stored in the working memory 540.

Figure 6A:
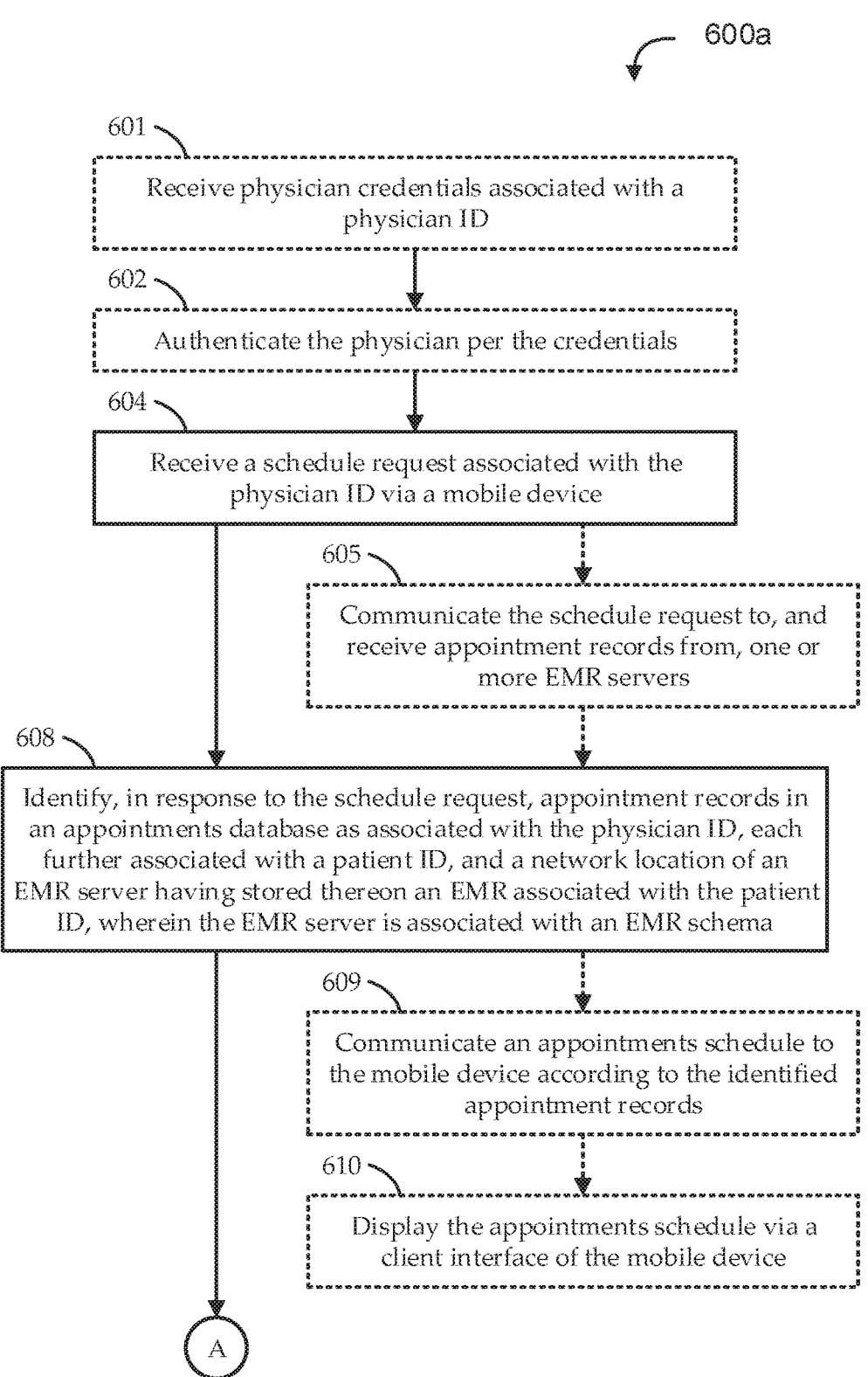
Figure 7:
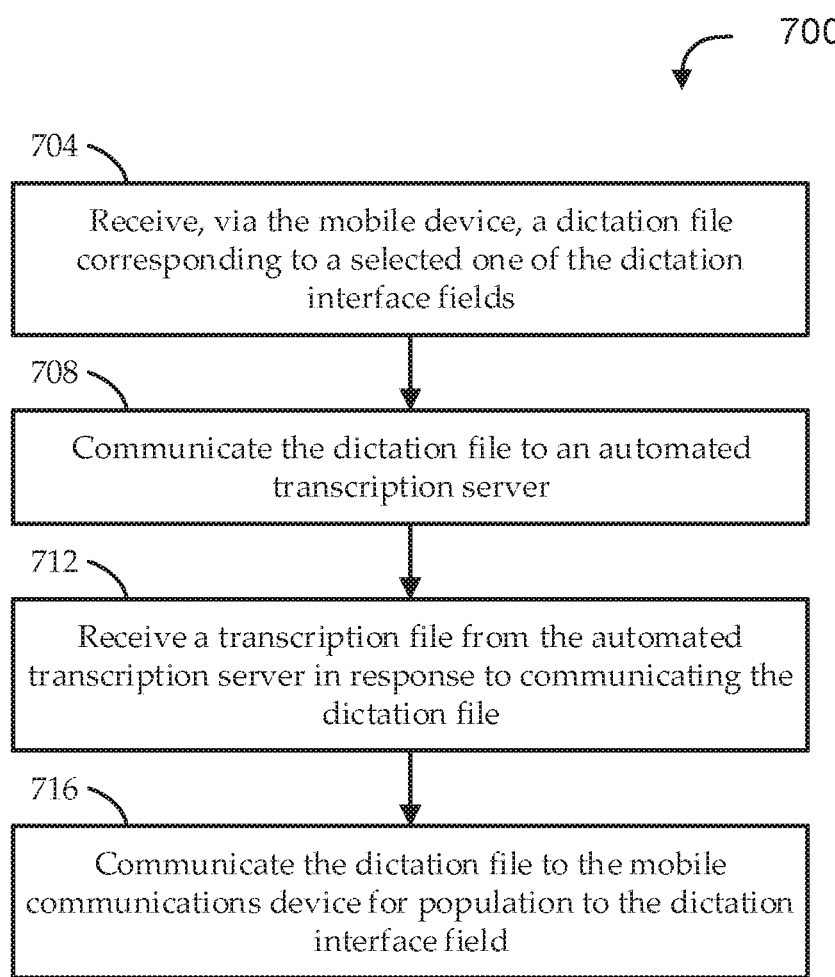
FIG. 7 shows a flow diagram of an illustrative method for receiving and transcribing dictation audio, according to various embodiments.

For the sake of added clarity, capabilities of the various system components are described more fully herein in context of various illustrative flow diagrams in FIGS. 6A, 6B, and 7. While certain embodiments are described in a manner that ascribes certain functionality to certain components, it will be appreciated that such descriptions are not intended to limit performance of method steps to particular components or component architectures.

FIGS. 6A and 6B show a flow diagram of an illustrative method 600 for interfacing with electronic medical records (EMR) over a communications network, according to various embodiments. Turning first to FIG. 6A, some embodiments of the method 600a can begin by authenticating the user (e.g., physician) of a client interface application (running on a smart phone, tablet computer, or other mobile interface device), through which the user desires EMR access. At stage 601, embodiments can receive physician credentials associated with a physician identifier. At stage 602, the physician can be authenticated according to the credentials. As described above, the authentication can be performed in a number of ways, including by the mobile interface devices, by the client interface applications, by an EMR proxy subsystem, by one or more EMR servers, etc. In some embodiments, the physician can be authenticated by affiliation to an authenticated group. For example, a physician can be authenticated as a referring physician, as a partner in a medical practice, as a physician with patient privileges at a facility, etc.

At stage 604, embodiments can receive (e.g., via the mobile interface device), a schedule request associated with the physician identifier. For example, the request can be for a current (e.g., daily) schedule, or for any past or future schedule. At stage 608, embodiments can identify, in response to the schedule request, appointment records in an appointments database as associated with the physician identifier. As described above, each appointment record can be further associated with a patient identifier, and a network location of an EMR server having stored thereon an EMR associated with the patient identifier. Also, each EMR server can be associated with an EMR schema that defines how EMR data is stored in the server and/or interface parameters for the EMR server. In some implementations, some or all of the appointment records are stored by the EMR servers (e.g., where the physician works with multiple facilities and/or organizations). In such implementations, identifying the appointment records for the physician at stage 608 can involve communicating the schedule request to, and receiving appointment records from, one or more EMR servers at stage 605.

Some embodiments continue by displaying the schedule and appointments to the requesting mobile interface device. For example, at stage 609, an appointments schedule can be communicated to the mobile interface device in accordance with the appointment records identified in stage 608. At stage 610, the appointments schedule can be displayed via the client interface application of the requesting mobile interface device (e.g., on a schedule interface screen, or the like).

Turning to FIG. 6B (i.e., following page reference "A"), embodiments of the method 600b can continue by receiving, via the mobile interface device, an appointment request indicating a selected one of the appointment records at stage 612a. At stage 616, a number of EMR field requests can be generated, each mapping one of a number of dictation interface fields to a corresponding EMR field of the EMR server associated with the selected appointment record according to the EMR schema associated with the EMR server. At stage 620, a patient record request corresponding to the selected appointment record can be communicated to the associated EMR server via the communications network according to the associated network location. The patient record request can include the associated patient identifier and the EMR field requests. As illustrated, in some implementations, the EMR field requests can be generated at stage 616, and/or the patient record request can be communicated at stage 620, prior to receiving the appointment request. Such cases illustrate the subsequent appointment request as stage 612b. For example, the EMR proxy subsystem can begin to pre-populate local EMR data (e.g., in a local EMR data store and/or in a cache of the mobile interface device)

for use by the client interface application. For example, such an approach can reduce any latency between selecting an appointment or field identifier, and receiving populated field data from the EMR servers. However, such an approach can risk providing the physician with stale data (e.g., data that has changed between the time it was pre-populated and the time it is viewed. Further, such an approach can risk accessing the EMR more than necessary, for example, if the physician does not ultimately view the pre-populated data. Accordingly, such approaches can include techniques for monitoring the freshness of the data, for estimating a likelihood of access to the data by the physician, etc.

Embodiments can continue at stage 624 by receiving, from the EMR server via the communications network, a number of EMR field responses in response to the EMR field requests. At stage 628, the EMR field responses can be communicated to the mobile interface device for display in corresponding dictation interface fields (associated with the appointment request). For example, the EMR field responses can be mapped, according to the appropriate EMR schema to the proper dictation fields, so that the dictation fields are populated with fresh data from the EMR server.

As described above, populating the data can include automatically transcribing dictated audio from the physician. FIG. 7 shows a flow diagram of an illustrative method 700 for receiving and transcribing dictation audio, according to various embodiments. Embodiments of the method 700 begin at stage 704 by receiving, via the mobile interface device, a dictation file corresponding to a selected one of the dictation interface fields. At stage 708, the dictation file can be communicated to an automated transcription server. A transcription file can be received from the automated transcription server at stage 712 in response to communicating the dictation file. For example, the transcription file can be a textual representation of the dictated audio. The transcription file can be communicated to the mobile interface device at stage 716 for population to the dictation interface field.

The methods described above can be implemented using any of the systems described above (e.g., with reference to FIG. 1) and/or other system implementations; and the systems described above can implement methods other than those described above. Further, some of the functions of the methods and systems described herein can be implemented in one or more computational environments, such as those described above with reference to FIG. 5.

The methods disclosed herein include one or more actions for achieving the described method. The method and/or actions may be interchanged with one another without departing from the scope of the claims. In other words, unless a specific order of actions is specified, the order and/or use of specific actions may be modified without departing from the scope of the claims.

Other examples and implementations are within the scope and spirit of the disclosure and appended claims. For example, features implementing functions may also be physically located at various positions, including being distributed such that portions of functions are implemented at different physical locations. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C). Further, the term "exemplary" does not mean that the described example is preferred or better than other examples.

Various changes, substitutions, and alterations to the techniques described herein can be made without departing from the technology of the teachings as defined by the appended claims. Moreover, the scope of the disclosure and claims is not limited to the particular aspects of the process, machine, manufacture, composition of matter, means, methods, and actions described above. Processes, machines, manufacture, compositions of matter, means, methods, or actions, presently existing or later to be developed, that perform substantially the same function or achieve substantially the same result as the corresponding aspects described herein may be utilized. Accordingly, the appended claims include within their scope such processes, machines, manufacture, compositions of matter, means, methods, or actions.

What is claimed is:

1. A method for interfacing with electronic medical records (EMR) over a communications network, the method comprising: associating a physician identifier with one or more of a user preference information, a schedule preference information, or a healthcare association information; selecting a first EMR server and a second EMR server from a plurality of EMR servers based on the physician identifier and access privileges associated with the physician identifier, wherein the physician identifier is registered with the first EMR server and the second EMR server, wherein the access privileges provide full access to the first EMR server and the second EMR server, wherein the full access to the first EMR server and the second EMR server includes access to read patient medical information from and write the patient medical information to the first EMR server and the second EMR server; receiving, via a mobile communications device, a schedule request associated with the physician identifier; identifying, in response to the schedule request, a plurality of appointment records in an appointments database as associated with the physician identifier, each appointment record further associated with a patient identifier, and a network location of an EMR server having stored thereon an EMR associated with the patient identifier, wherein the EMR server is associated with an EMR schema; generating a schedule interface for the physician identifier based on the plurality of appointment records and the associated one or more of the user preference information, the schedule preference information, or the healthcare association information, the schedule interface displaying a first appointment record of the plurality of appointment records having at least one field populated with data from the first EMR server and a second appointment record of the plurality of appointment records having at least one field populated with data from the second EMR server, wherein the first appointment record and the second appointment record are displayed at one time at the schedule interface; receiving, via the mobile communications device, an appointment request indicating a selected one of the appointment records, the selected one of the appointment records selected from the schedule interface; generating a plurality of EMR field requests, each mapping one of a plurality of dictation interface fields to a corresponding EMR field of the EMR server associated with the selected appointment record according to the EMR schema associated with the EMR server; communicating a patient record request corresponding to the selected appointment record, the patient record request communicated to the associated EMR server via the communications network according to the associated network location, and the patient record request comprising the associated patient identifier and the plurality of EMR field requests; receiving, from the EMR server via the communications network, a plurality of EMR field responses in response to the plurality of EMR field requests; and communicating the plurality of EMR field responses to the mobile communications device for display in the dictation interface fields in association with the appointment request, wherein at least one of the plurality of appointment records is identified as associated with the physician identifier by being identified as associated with a physician organization that comprises a physician corresponding to the physician identifier.

\* \* \* \* \*